United States Patent [19]

Blocquel et al.

[11] Patent Number: 5,268,550

[45] Date of Patent: Dec. 7, 1993

[54] METHOD AND DEVICE FOR REMOVING A SPECIMEN FROM WITHIN THE VESSEL OF A NUCLEAR REACTOR BEING DECOMMISSIONED

[75] Inventors: Alain Blocquel, Dardilly; Joseph Lara, Montanay, both of France

[73] Assignee: Framatome, Courbevoie, France

[21] Appl. No.: 964,306

[22] Filed: Oct. 21, 1992

[30] Foreign Application Priority Data

Oct. 21, 1991 [FR] France .................. 91 12975

[51] Int. Cl.⁵ .............................................. B23H 9/00
[52] U.S. Cl. .................. 219/69.17; 219/69.2; 376/260
[58] Field of Search ............. 219/69.11, 69.2, 69.17; 376/260, 262

[56] References Cited

U.S. PATENT DOCUMENTS

| | | | |
|---|---|---|---|
| 3,910,138 | 10/1975 | Sinha et al. | 76/107.8 |
| 4,405,430 | 9/1983 | Hanulik | 204/400 |
| 5,209,895 | 5/1993 | Wivagg | 376/260 |
| 5,225,645 | 7/1993 | Overbay et al. | 219/69.11 |

FOREIGN PATENT DOCUMENTS

| | | | |
|---|---|---|---|
| 0247205 | 6/1987 | European Pat. Off. | |
| 0451015 | 10/1991 | European Pat. Off. | |
| 56-82126 | 7/1981 | Japan | 219/69.17 |
| 61-90098 | 5/1986 | Japan | 376/260 |
| 62-263865 | 11/1987 | Japan | 219/69.2 |

OTHER PUBLICATIONS

"Performance of the Automated Cutting Equipment System During the Plasma Cutting of the Three Mile Island Unit 2 Lower Core Support Assembly", pp. 648–659, by McGough et al., *Nuclear Technology*, Nov. 1989.

"Underwater Arc Saw Gets to Work on the Vessel at Japan's JPDR", pp. 35–36 of Nuclear Engineering International,. Sep. 1990 by Yokota et al.

"At The Cutting Edge", pp. 32–33 of Nuclear Engineering International, Jul. 1989.

*Primary Examiner*—Geoffrey S. Evans
*Attorney, Agent, or Firm*—Pollock, Vande Sande & Priddy

[57] ABSTRACT

A method and device for removal of a specimen (30), especially a parallelepipedal specimen, from within the internal wall of the vessel of a nuclear reactor which is at the end of its service and whose core has previously been dismantled, but which retains a high residual radioactivity. A rotating platform (10) carrying tools (23, 24) for cutting out by electrical discharge is inserted into the vessel (1), maintained under protective water (7). A first electrode produces a recess in a direction perpendicular to the internal wall (21) of the vessel, delimiting the external contour of the specimen, and a second electrode cuts the rear of the latter to a specified depth, before the withdrawal thereof from the wall. The specimen thus obtained is then extracted from the vessel.

10 Claims, 6 Drawing Sheets

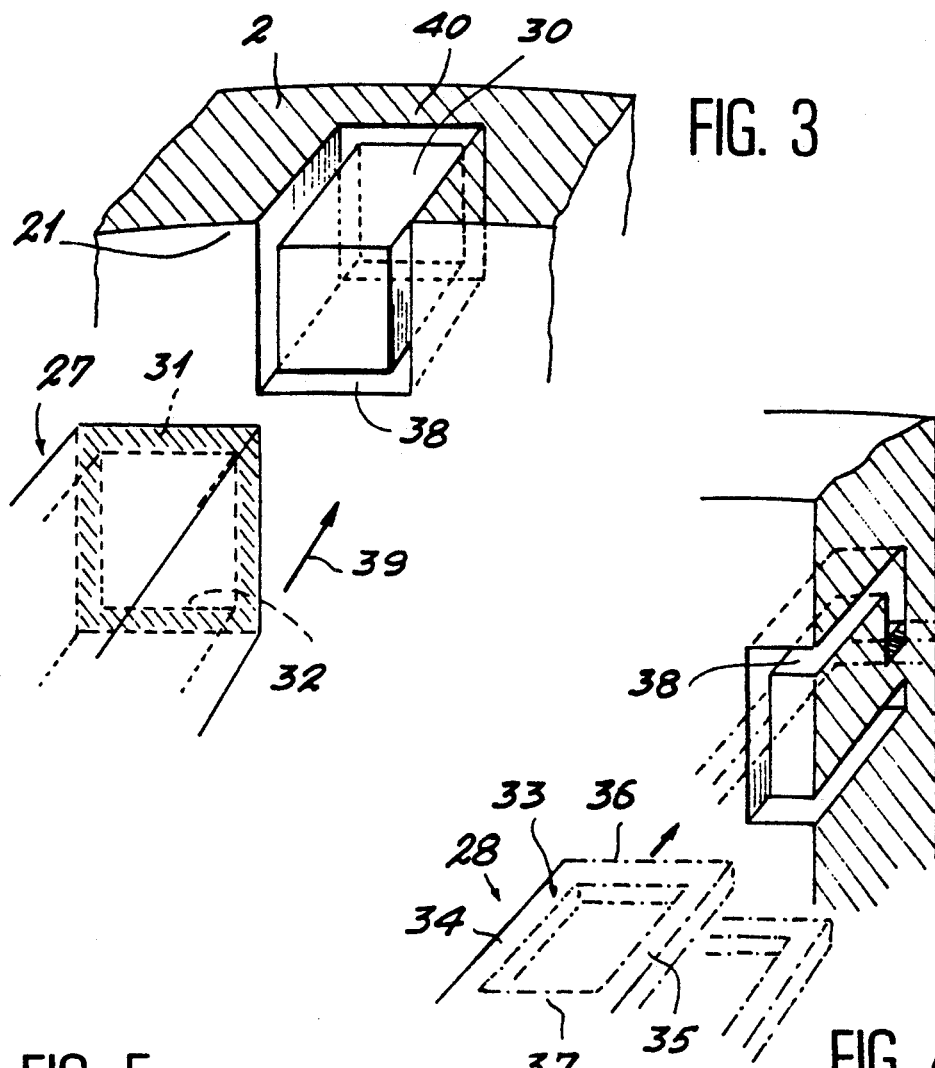
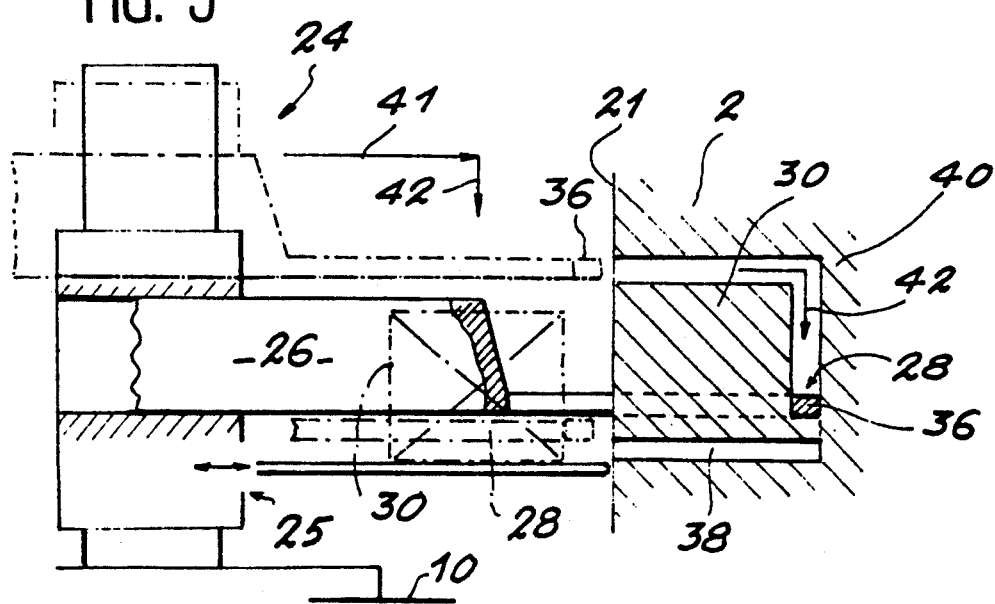

METHOD AND DEVICE FOR REMOVING A SPECIMEN FROM WITHIN THE VESSEL OF A NUCLEAR REACTOR BEING DECOMMISSIONED

FIELD OF THE INVENTION

The present invention relates to a method and to a device for the removal of a monitoring specimen from within the wall of the vessel of a nuclear reactor being decommissioned.

BACKGROUND OF THE INVENTION

It is known that at present, the average lifetime of a nuclear reactor is, of the order of some twenty years, as the continuous irradiation of the structures of such a facility and the fatigue of the materials make it impossible, in principle, to maintain the reactor in operation and, especially in production, beyond this period. Because of the very strong residual radioactivity which remains after the final shutdown of the reactor, it is still advisable to maintain certain parts of the latter, in particular the vessel which surrounds the core itself, after dismantling the latter by way of its elements, under suitable protection, in particular by leaving the vessel filled with water for a very long period.

However, it is understood that, under these conditions, it is necessary to monitor continuously certain characteristics of the metal material, generally special steel, which constitutes the vessel, in order to know how it behaves under prolonged irradiation under circumstances thus envisaged for the storage and prolonged preservation of the vessel. With this objective in mind, it is necessary to make use of specimens of the highly-irradiated metal constituting the wall of the vessel, enabling its transformation to be followed, in particular its rate of embrittlement which increases over time, in such a way as to inspect the behavior of the vessel with respect to pressure and temperature stresses which it continues to undergo because of the presence of the volume of water which it contains and of the vessel with respect to pressure and temperature stresses which it continues to undergo because of the presence of the volume of water which it contains and of the external climatic conditions. Moreover, the study of such specimens enables useful conclusions to be drawn as regards the improvements which can be made to the nature of the metal to be used for future reactors, by improving the safety conditions for the latter and above all the possible utilization times, in such a manner as to improve the return on the considerable financial investments which they represent.

Moreover, it is understood that the removal of significant specimens from within the very thickness of the vessel, via the inside of the latter, must be carried out with extreme precision, in such a way as not to undermine, beyond strict limits, the integrity of the vessel which remains filled with the protective water which has a certain activity and leakage of which towards the outside must be rigorously avoided.

SUMMARY OF THE INVENTION

With this objective in mind, the invention relates to out a method which permits such removal to be carried out by meeting these essential requirements, especially by allowing parallelepipedal specimens or samples of strictly specified dimension to be removed, these being withdrawn directly from the internal wall of the vessel without piercing the latter, which is damaged only within precise and strictly controlled limits. The invention also relates to a device suitable for carrying out this method.

For this purpose, the method in question, for removing at least one sample of specified shape, especially parallelepipedal, from within the wall of a vessel of generally cylindrical vessel having a vertical general shape having a vertical axis, of a nuclear reactor being decommissioned, which vessel is maintained under protective water, from the internal surface of the vessel and preferably from within a deep-down region of the latter where the irradiation by the core of the reactor in operation was the most intense, consists in vertically lowering, along the axis of the vessel which is open at the top, a support of a horizontal rotating platform, comprising means suitable for temporarily securing it with respect to the internal wall of the vessel, and in remotely actuating the displacement of tools for cutting out a portion of the thickness of the vessel, in particular by electrical-discharge machining. The tools are carried by the rotating platform, so as to form the specimen within the thickness of the wall, following a movement of penetration of a first electrode perpendicular to the wall, producing a recess which delimits the external rectangular contour of this specimen, and then of a second electrode penetrating into one of the sides of the recess created by the first electrode in order then to be displaced in the direction of the opposite side, so as to complete the cutting-out of the specimen which remains secured to the second electrode after the displacement of the latter during its withdrawal from the wall of the vessel.

The device for permitting the method to be is characterised, for its part, in that it comprises a support for a rotating platform provided with means of immobilization with respect to the internal wall of the vessel in the vicinity of a zone from which the metal of the vessel is to be removed. The device further comprises a first tool for machining, especially by electrical discharge, comprising a first hollow electrode, of rectangular cross-section, carried by a positioning mandrel suitable for imposing on the electrode a forward or reverse movement perpendicular to the wall in order to create a continuous recess delimiting, on four sides, the external contour of a parallelepipedal specimen. The device further comprises a second tool for machining, also be electrical discharge, comprising a second plate-shaped electrode, comprising a rectangular-profiled central housing whose dimension are equal to those of the transverse cross-section of the parallelepipedal specimen to be removed, this second electrode being carried by another positioning mandrel, suitable for providing the insertion of this electrode into one of the sides of the recess created by the first electrode, then for displacing the second electrode perpendicular to the direction of its forward movement towards the side opposite the recess and then for withdrawing the specimen thus cut out with the second electrode. The rotating platform carries means for successively indexing the positions of the mandrels carrying the first and second electrodes with respect to the zone for removing the specimen, thereby permitting the release of one of the mandrels when the other actuates the displacements of the associated specimen, and vice versa, and, finally, means for withdrawing the cut-out specimen from the second electrode and extracting it from the vessel.

According to the particular feature of the inventing device, the rotating platform rests plane on plane on its support, the latter being capable of being displaced in the vessel along the vertical axis of the vessel, and comprising means of immobilization opposite the zone for removing the specimen. Advantageously, and in a preferred embodiment of the invention, the means of immobilization are constituted by locking thrust cylinders, whose bodies are carried by the support structure and whose movable rods have ends provided, at with feet for bearing against the internal wall of the vessel, these thrust cylinders being distributed symmetrically about the vertical axis of the vessel.

According to another feature of the invention, the support comprises a vertical central mast provided which is vertical and provided at its upper end with a lug enabling it to be clamped by a suspension sling, capable of enabling the support and the rotating platform which it supports to be raised or lowered within the vessel.

According to yet another characteristic, the rotating platform carried by the support has an angular-sector profile and comprises a guide swivelling in an axial bearing carried by the vertical mast, such that the platform can be oriented into any position about the axis of the vessel. In a preferred embodiment of the invention, the rotating platform occupies is provided for occupying in four successive separate positions, disposed respectively at 90° to each other about the vertical axis, with respect to the internal wall of the vessel.

The first electrode having a rectangular cross-section preferably matches the shape of a hollow sleeve, the bottom of which is solidly connected to the mandrel for actuating forward or its reverse movement, perpendicular to the internal all of the vessel. The second electrode is flat and has a height substantially equal to the thickness of the recess created by the first electrode, the central housing of the second electrode being delimited by two parallel crosspieces separated by a distance equal to the depth of the specimen to be removed.

Also according to another characteristic. The means for withdrawing the specimen from the second electrode, after withdrawal of the latter from the recess created by the first electrode, comprise a pole or the like provided at its end with a gripper whose jaws are remotely actuated, the displacement of the gripper being carried out preferably parallel to the vertical axis of the vessel above the rotating platform, between the second electrode and a container for receiving and transporting the specimen removed.

BRIEF DESCRIPTION OF THE DRAWINGS

Other characteristics of a method and of a device for removing at least one metal specimen, especially a parallelepipedal specimen, from within the wall of the vessel of a nuclear reactor will appear in the description which follows of an exemplary embodiment, given by way of example, with reference to the attached drawings in which:

FIG. 3 is a perspective view, on a larger scale, illustrating the profile and the method of utilizing a first electrode, necessary according to the invention for producing the specimen to be removed from within the wall of the vessel.

FIG. 4 is a perspective view, similar to FIG. 3, but relating to the profile of the second electrode, illustrating the manner of using the latter.

FIG. 5 is another view, in longitudinal cross-section, of the second electrode and of the means associated with the latter in order to actuate its movements.

DESCRIPTION OF PREFERRED EMBODIMENT

Figure 1:
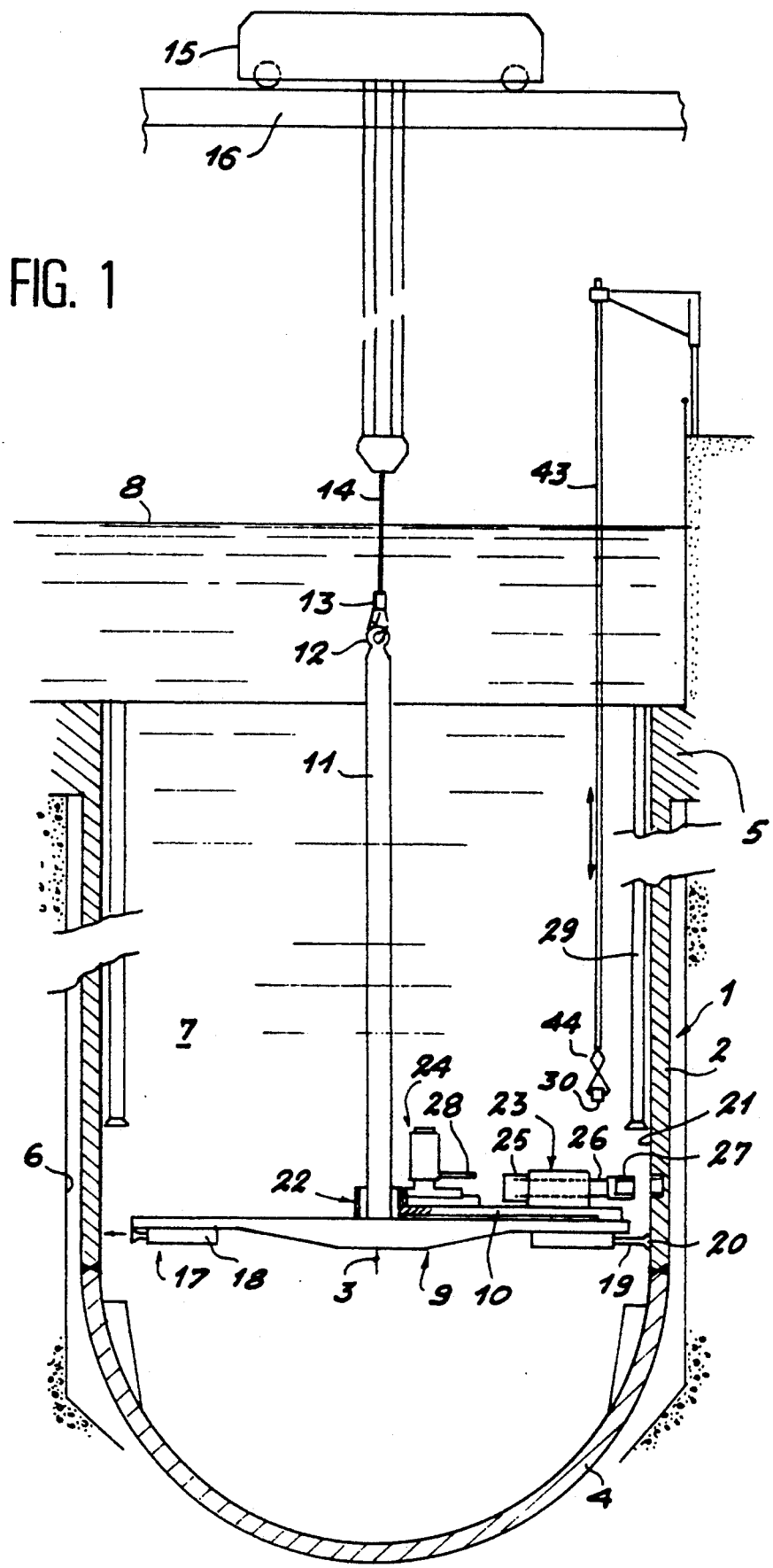
FIG. 1 is a schematic view, in vertical axial cross-section of a cylindrical vessel for a nuclear reactor, containing means which, in accordance with the invention, permit to be removed from within the wall of the vessel at least one specimen or sample of the metal material which constitutes it.

As shown in FIG. 1, reference 1 designates a conventional vessel of a nuclear reactor, comprises a generally cylindrical lateral shell 2, axisymmetric about a vertical axis 3, the lower end of this shell being closed off by a substantially spherical cap 4, also centered on the axis 3. The upper part of shell 2 comprises a flange 5 for bearing on a concrete protective outer casing 6, surrounding the shell and the lower cap, this flange serving especially as a support, during the operation of the reactor, for a plate for covering the vessel above the core contained in the latter.

The shell 2 is made from an appropriate metal material, generally from a special steel, and has a suitable thickness so as in particular to impart to it a mechanical strength sufficient to oppose forces and stresses which it experiences during the operation of the reactor.

The present invention comes into play under particular circumstances when the nuclear reactor is decommissioned and extracted from the vessel 1, by way of its elements, thereby leaving free the space internal to the shell 2, the vessel being entirely filled with an internal volume of water 7 enabling the outer environment to be satisfactorily protected in terms of radiation emanating from the still very highly irradiated walls of the vessel.

To continuously monitor the changes in the characteristics of the metal constituting the wall of the vessel during the long time indispensable for an acceptable decrease of the released radioactivity, it turns out to be necessary to be able to remove specimens from the metal of the vessel at least at one given instant, or indeed repetitively at specified intervals of time, this removal having to be carried out without undermining the integrity of the containment of the protective water, the analysis of these specimens enabling precious information to be drawn on the behavior of the metal under the conditions thus envisaged.

With this objective in mind and according to the invention, a support 9 which extends horizontally across the vessel and which itself carries a rotating platform 10, the role of which will be defined later, is introduced along the vertical axis of this vessel and the superstructures of the reactor. This support 9 comprises a vertical mast 11, provided at its upper part with a suspension lug 12 to which is fixed a shackle or another hitching means 13 fixed to the end of a sling 14, unwound from a handling winch 15 carried by a travelling crane 16 extending above the open upper part of the vessel 1.

The support 9 is provided, on its periphery, with several thrust cylinders 17, the bodies 18 of which are radially disposed beneath the support and immobilized with respect to the latter, the movable rod 19 of each thrust cylinder being provided at its end with a bearing foot 20 enabling the support to be locked with respect to the internal wall 21 of the shell 2, the thrust cylinders 17 being advantageously and uniformly distributed about the vertical axis 3 of the shell, coincident with the vertical mast 11 lowering the support 9 into the shell.

Figure 2:
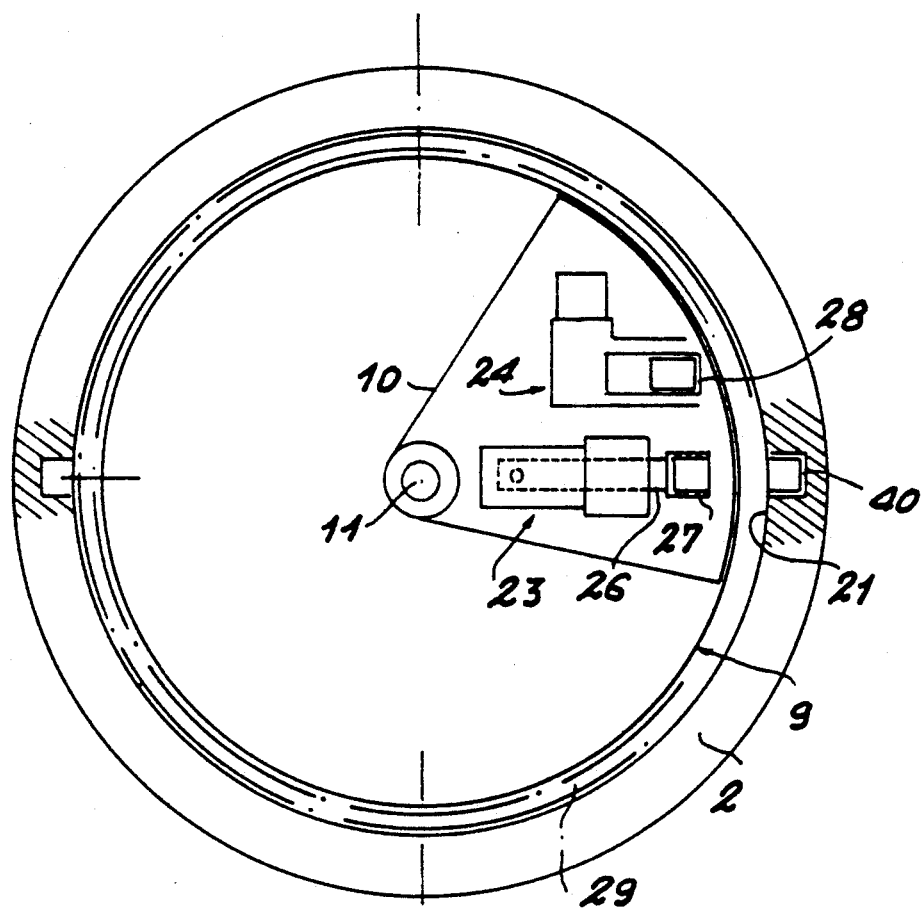
FIG. 2 is a view, in transverse cross-section along a plane perpendicular to its axis, of the reactor vessel illustrated in FIG. 1.

The horizontal rotating platform 10 carried by the support 9 comprises a guide 22, engaging with the lower end of the mast 11 so as to enable the platform to be oriented in any direction about the vertical axis 3, this platform preferably having an angular-sector profile, as shown more particularly in FIG. 2.

Moreover, on the platform 10 are mounted two separate machining tools, respectively designated in FIGS. 1 and 2 by the references 23 and 24, these tools each comprising a support-frame 25 for the displacement, in a direction substantially perpendicular to the internal wall 21, of a mandrel 26 forming an electrode holder.

The machining tools 23 and 24 are preferably constituted by electrical-discharge machining devices enabling a first electrode 27 and then a second electrode 28 especially made from graphite, which electrodes ar respectively carried by each of these devices, to remove a specimen of specified shape and size, especially parallelepipedal, from within the internal wall 21 of the shell 2, this removal preferably being carried out from within a relatively deep part of the vessel, in the zone of the latter which was located opposite the core during the operation of the reactor, in particular under a thermal shield 29 which, possibly but not exclusively, may be provided within the shell 2 parallel to the latter.

FIGS. 3 to 5 show in greater detail the structure of the electrodes 27 and 28 producing in the shell 2, from its internal wall 21, the formation and then the removal of the parallelepipedal specimen 30. As shown in FIG. 3, electrode 27 has a hollow sleeve-shaped profile 31 with internal cavity 32 of square or rectangular cross-section, the contour of the sleeve corresponding to the outer profile of the specimen 30 to be removed from within the wall. The second electrode 28 has the shape of a frame 33 whose lateral sides 34 and 35 are separated by a distance equal to the width of the specimen 30, these sides being joined together by two crosspieces, respectively 36 and 37, which are themselves separated by a distance equal to the depth of the specimen, the thickness of the frame 33 being equal to the height of the recess 38 delimited, around the specimen 30 in the wall of the shell 2, by the penetration into the latter of the first electrode 27.

In FIG. 3, the arrow 39 represents schematically the displacement movement capable of being imposed on the first electrode 27 in relation to the internal wall 21 of the shell 2, when the rotating platform 10 and the machining tool 23 carrying this electrode are suitably positioned opposite this wall, the displacement of the electrode being carried out in a direction substantially perpendicular to this wall. Under these conditions, the electrode 27 progressively penetrates into the wall, thereby making, around the body of the specimen 30 to be removed, the recess 38, the forward movement of this electrode being carried out over a specified depth, which leaves, in every case at the bottom of the recess a thickness of metal or remaining wall 40 sufficient for avoiding any risk of piercing of the shell 2 of the wall, which may thus permanently withstand the pressure of the protective water which it contains. In practice, the depth of penetration of the first electrode 27 into the wall of the shell 2, which equals the height of the specimen 30, is never greater than 4/5ths of total thickness of the wall, this ratio being given only by way of indication.

In FIG. 5, shows schematically the second electrode 28 carried by the actuating mandrel 26, movable in the support-frame 25 of the corresponding machining tool 23, this support-frame being so arranged that it enables the electrode 28, in this case frame-shaped, to perform a first penetration movement within the recess along the direction of the arrow 41 and then, when the crosspeice 36 abuts against the bottom of this recess, substantially in contact with the remaining wall 40, a second displacement in the direction of the arrow 42, preferably from the top downwards as shown in this figure, in such a way as then to cut out the specimen 30 behind the latter, between the specimen and the remaining wall, thereby enabling the specimen to be finally detached from the wall of the shell 2.

The movement of the second electrode 28 is advantageously carried out such that, at the end of downward travel separating the specimen from the wall, the frame 33 continues to surround the specimen thus detached in order to enable, subsequently, by means of a withdrawing movement in the reverse direction of the forward movement along the arrow 42, the electrode 28 to be withdrawn at the same time as the specimen 30 (shown as dot-dash lines), as far as a position where the latter may finally be extracted from the vessel, preferably parallel to the axis 3, by means of a pole 43 provided at its end with a clamping gripper 44 (see FIG. 1) or with any other similar means, before being deposited in a container (not shown).

FIGS. 6 to 11 permit a better understanding of the manner of proceeding, according to the invention, in order to perform by means of a suitable indexation of the rotating platform 10 with respect to the internal wall 21 of the shell 2 of the vessel 1, the removal of one, or indeed of several specimens 30 in succession, these removals being preferably performed at four locations distributed at 90° to each other from within the shell right opposite the location chosen for the immobilization of the support 9 by virtue of the locking feet 20 (FIG. 1). It should be noted that the thrust cylinders 17 which actuate these feet are provided such that, in the retracted position of their rods 19, the overall size of the support 9 is sufficiently limited in order to not to impede its descent into the vessel right opposite the thermal shield 29, before this support is firmly immobilized against the shell beneath this shield as a consequence of the extension of the thrust cylinder.

Figure 6:
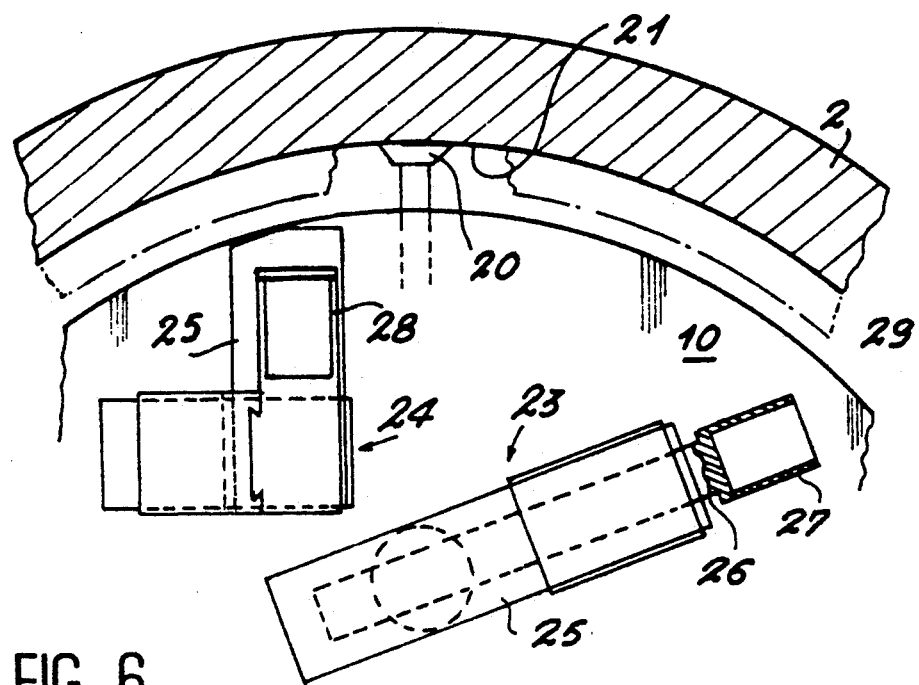
FIGS. 6 to 11 are schematic views, in transverse cross-section, which show the succession of steps for using the two electrodes in order to cut out and extract a specimen removed from within the wall of the vessel of the reactor by means of these two electrodes.

In FIG. 6, the two electrical-discharge machining tools 23 and 24 are in an inactive position during the azimuthal positioning of the rotating platform 10, this positioning being carried out very precisely, once the support 9 has been previously installed at the chosen level along the vertical axis 3 of the vessel, by indexation with respect to suitable reference points provided in the internal surface 21, before finally locking the platform.

Figure 7:
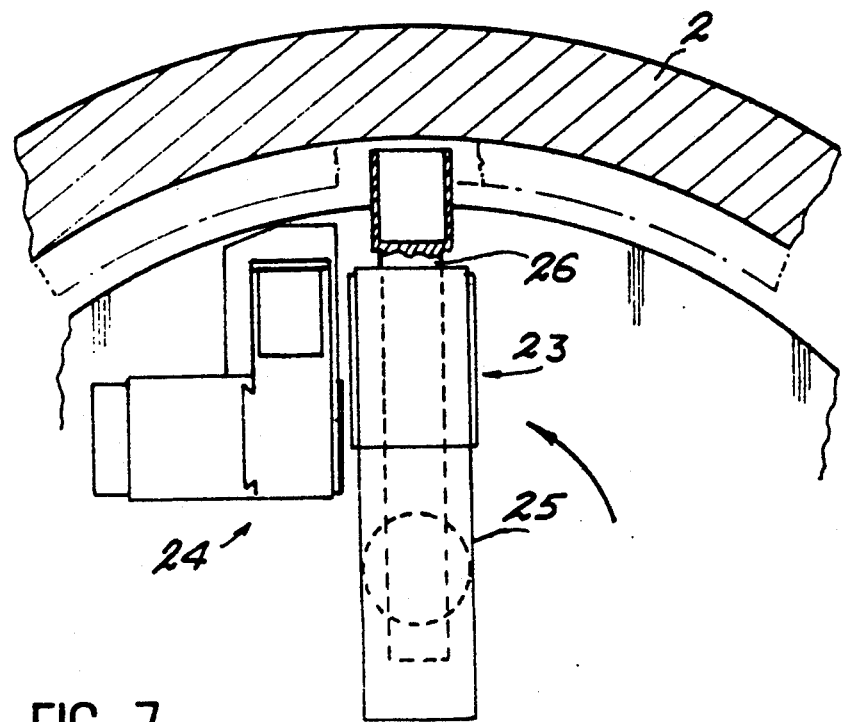

In FIG. 7, the tool 24 is out of operation, whereas the tool 23 is actuated such that is support-frame 25 is placed opposite the wall 21, its actuating mandrel 26 being directed perpendicularly to the latter.

Figure 8:
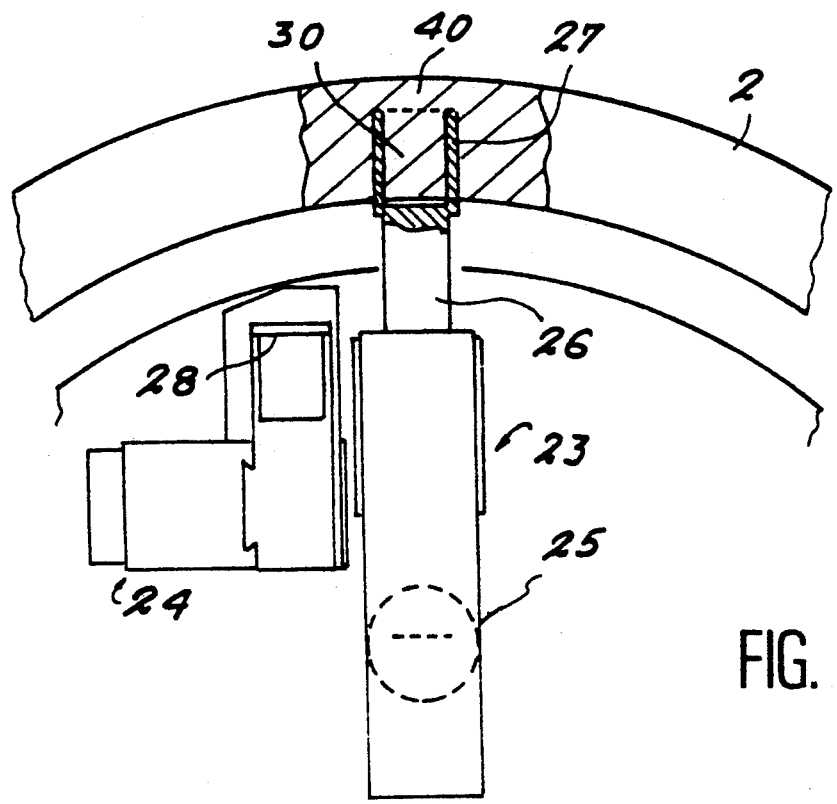

In the following phase, illustrated in FIG. 8, the first electrode 27 penetrates into the thickness of the shell 2 over a suitable depth corresponding to the height of the specimen 30 to be produced, the mandrel 26 being displaced parallel to itself in order to cause the electrode to move forward into the wall, thereby delimiting, within the hollow sleeve of this electrode, the profile of the specimen, while leaving behind the latter a suitable wall thickness corresponding to the remaining wall 40.

Figure 9:
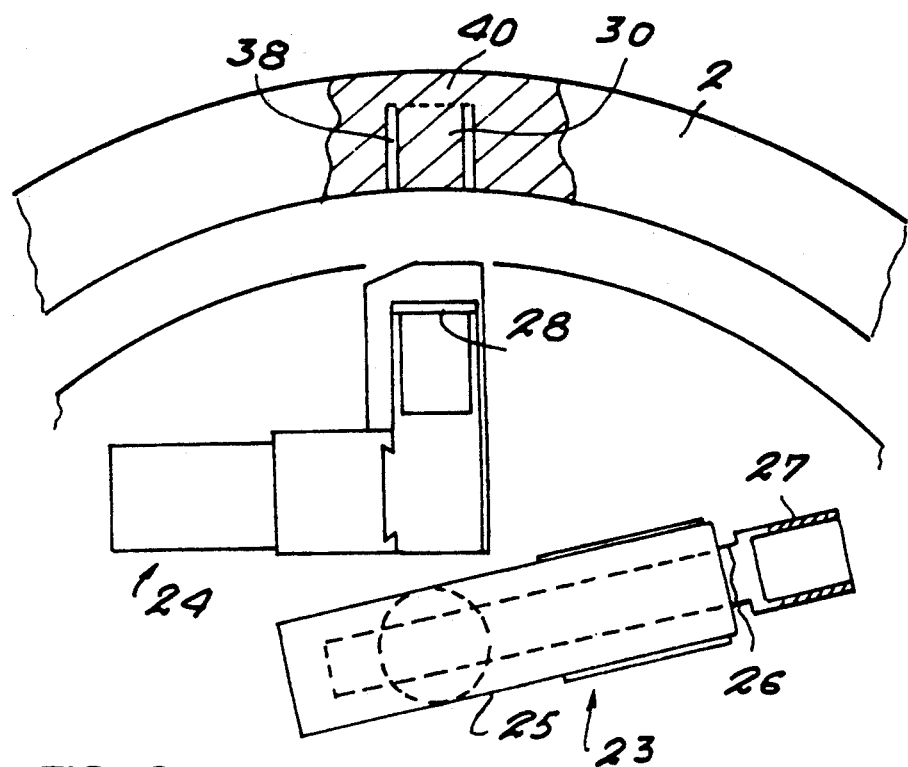

In the following step, the mandrel 26 performs a withdrawal movement causing the electrode 27 to leave the recess 38 which it has made in the thickness of the vessel, the support-frame 25 then being pivoted on the platform 10 so as to enable the other tool 24 to be displaced and the second electrode 28 to be put into place opposite this recess (FIG. 9).

Figure 10:
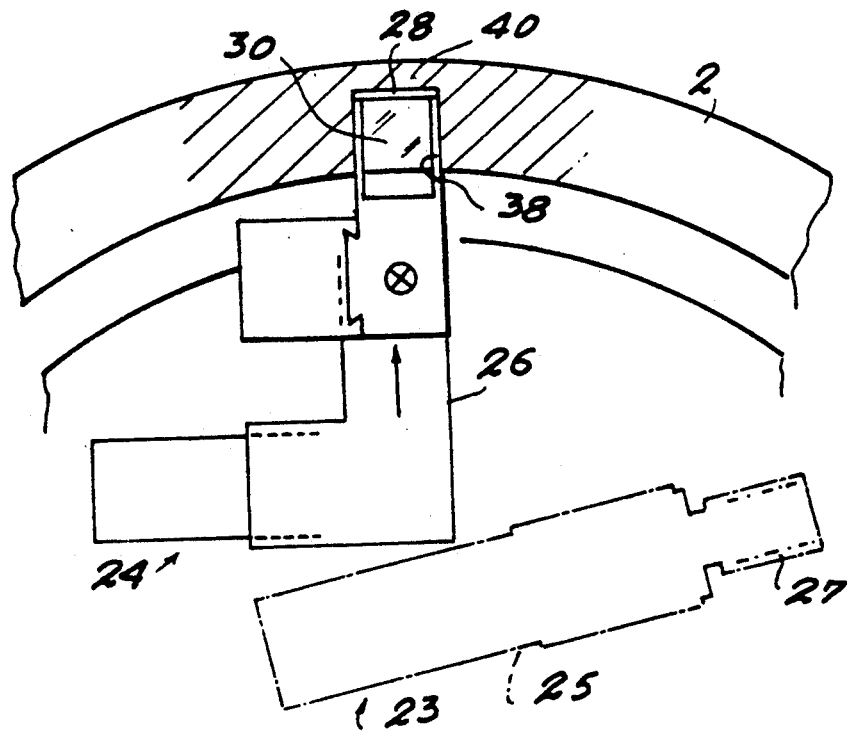
Figure 11:
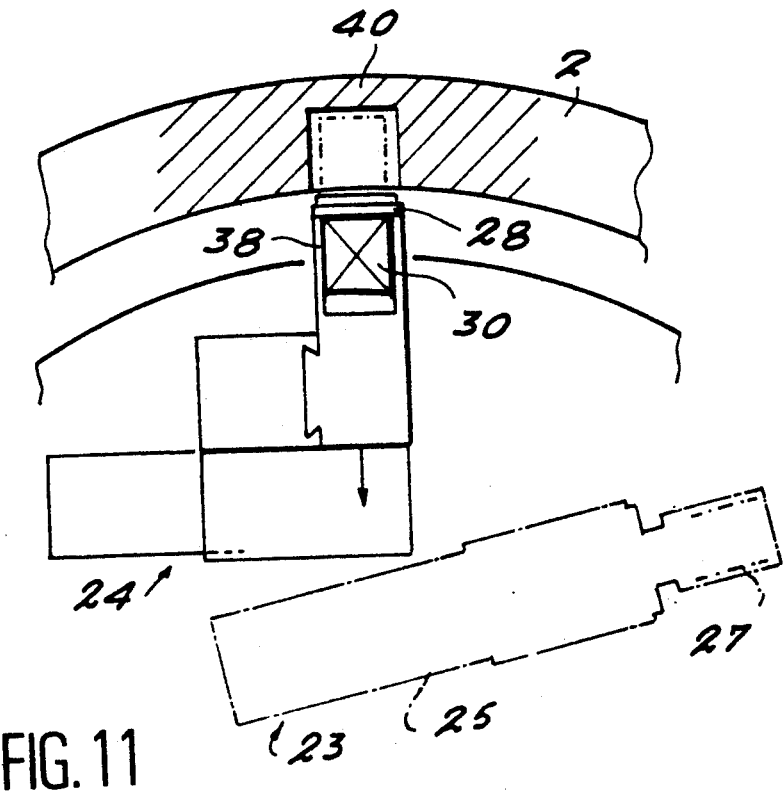

The latter electrode is then engaged into the recess substantially until it contacts the remaining wall 40 and the perform a downward movement, preferably from the top downwards, in order to cut off the specimen 30 before the latter is finally extracted from the wall of the shell by being entrained with the electrode 28 because of the frame-shaped profile of the latter (see FIGS. 10 and 11 in succession).

A device for removing a specimen from within the thick wall of the shell of the vessel of a nuclear reactor being decommissioned is thus produced, enabling extremely precise and safe machining of this specimen, under the most reliable and safest operating conditions.

The number of removals of such specimens may be as great as desired, although these removals are preferably limited to four, in each transverse plane where the support of the rotating platform is positioned, thereby being distributed in this plane along two perpendicular directions in which they form facing pairs.

The structure of the tools for machining by electrical discharge, as well as that of their actuating support-frame and of the mandrels producing the displacements of the electrodes, have not be described, as such devices and apparatuses are well known in the art. The same applies to the means necessary for actuating the rotational driving of the rotating platform 10 about the vertical mast 11, as well as to the devices enabling the positions for immobilizing the platform, opposite each location of the shell where the removal of a specimen is to be carried out, to be indexed, these means being within the knowledge of those skilled in the art and involving no unconventional solutions.

Finally, it also appears to be unnecessary to described in further detail the use of the devices schematically shown in the drawings for extracting or putting into place the support 9 of the platform 10 within the shell of the vessel, by means of the winch 15 and of the travelling crane 16, as well as the means for actuating the thrust cylinders 17 for immobilizing the support with respect to the shell 2. The displacement of the second electrode producing the cutting-out of the specimen may be carried out according to a top-down movement in the bottom of the recess created by the first electrode, or sides of this recess and displaced from right to left or from left to right depending on the case, i.e., in a direction perpendicular to the previous direction, therefore, in order to achieve the same result.

We claim:

1. Method for the removal of at least one sample or specimen (30) of specified shape from within the wall (2) of a generally cylindrical nuclear reactor vessel (1) having a vertical axis and an open top (3) and being maintained under protective water (7), from an internal wall surface (21) of said vessel, said method comprising the steps of (a) vertically lowering, along said axis of said vessel, a support (9) of a horizontal rotating platform (10), comprising means (17) suitable for temporarily securing it with respect to said internal wall of the vessel; and (b) remotely actuating the displacement of tools for cutting out (23, 24) a portion of a thickness of said vessel, said tools being carried by said rotating platform, so as to form the specimen (30) within the thickness of the wall, following a movement of penetration of a first electrode (27) perpendicular to the wall, producing a recess (31) which delimits an external rectangular contour of said specimen, and then of a second electrode (28) penetrating into a side of said recess created by said first electrode in order then to be displaced in a direction of an opposite side so as to complete cutting-out of said specimen which remains secured to said second electrode after displacement of said second electrode during its withdrawal from said wall of said vessel.

2. Device for the removal of at least one sample or specimen (3) of specified shape from within the wall (2) of a generally cylindrical nuclear reactor vessel (1) having a vertical axis and an open top (3) and being maintained under protective water( 7), from an internal wall surface (21) of said vessel, said device comprising a support (9) for a rotating platform (1) provided with means (17) of immobilization with respect to the internal wall (21) of the vessel (1) in the vicinity of a zone from which the metal of the vessel is to be removed, a first tool (23) for machining by electrical discharge, said first tool comprising a first hollow electrode &27) of rectangular cross-section, carried by a positioning mandrel (26) adapted to impose on the electrode a forward or reverse movement perpendicular to the wall in order to create a continuous recess (31) delimiting, on four sides, the external contour of a parallelepipedal specimen (3), a second tool (24) for machining, also by electrical discharge, said second tool comprising a second plate-shaped electrode (28) comprising a rectangular central housing having dimensions equal to the dimensions of the transverse cross-section of the parallelepipedal specimen to be removed, said second electrode being carried by another positioning mandrel adapted to insert said second electrode into one of the sides of the recess created by said first electrode, then for displacing said second electrode perpendicular to the direction of its forward movement towards the side opposite the recess and then for withdrawing the specimen thus cut out with said second electrode, means associated with the rotating platform for successively indexing the position of the mandrels carrying said first and second electrodes with respect to the zone for removing the specimen, thereby permitting the release of one of the mandrels when the other actuates the displacements of the associated specimen, and means (43, 44) for withdrawing the cut-out specimen from the second electrode and extracting it from the vessel.

3. Device according to clam 2, wherein the rotating platform (10) rests plane on plane on said support (9), said support being displaced in the vessel (1) along the vertical axis (3) of said vessel and comprising means of immobilization opposite the zone for removing the specimen.

4. Device according to claim 2 or 3, wherein the means of immobilization are constituted by locking thrust cylinders (17) having bodies (18) carried by the support and movable rods (19) provided at their ends with feet (2) for bearing against the internal wall (21) of the vessel, said thrust cylinders being distributed symmetrically about the vertical axis (3) of the vessel.

5. Device according to claim 2, wherein the support (9) comprises a central mast (11) which is vertical and which has an upper end provided with a lug (12) enabling it to be clamped by a suspension sling (14), capable of enabling the support and the rotating platform which it supports to be raised or lowered within the vessel.

6. Device according to claim 5, wherein the rotating platform (10) carried by the support (9) has an angular-sector profile and comprises a guide (22) swivelling in an axial bearing carried by the vertical mast (11) such that said platform can be oriented in any position about the axis of the vessel.

7. Device according to claim 6, wherein the rotating platform (10) is provided for occupying in succession four separate positions, disposed respectively at 90° to each other about the axis of the vessel, with respect to the internal wall of the vessel.

8. Device according to claim 2, wherein said first electrode (27) matches the shape of a hollow sleeve having a bottom which is solidly connected to the mandrel (26) for actuating its forward or its reverse movement, perpendicular to the internal wall (21) of the vessel.

9. Device according to claim 2, wherein said second electrode (28) is flat and has a height substantially equal to the thickness of the recess (31) created by the first electrode (27), the central housing of the second electrode being delimited by two parallel crosspieces separated by a distance equal to the depth of the specimen (30) to be removed.

10. Device according to claim 2, wherein the means for withdrawing the specimen from the second electrode, after withdrawal of the second electrode from the recess created by the first electrode, comprise pole means (43) provided at its end with a gripper (44) having remotely actuated jaws, the gripper being displaced parallel to the vertical axis (3) of the vessel above the rotating platform (10), between the second electrode (28) and a container for receiving and transporting the removed specimen (30).

* * * * *